United States Patent [19]

Cherney et al.

[11] Patent Number: 4,758,683
[45] Date of Patent: Jul. 19, 1988

[54] SPIRODIPHOSPHOAMIDATE COMPOUNDS

[75] Inventors: Lee Cherney, Arlington Hgts.; Yuval Halpern, Skokie, both of Ill.

[73] Assignee: Borg-Warner Chemicals, Inc., Parkersburg, W. Va.

[21] Appl. No.: 102,270

[22] Filed: Sep. 25, 1987

Related U.S. Application Data

[63] Continuation of Ser. No. 813,161, Dec. 24, 1985, abandoned.

[51] Int. Cl.⁴ .............................................. C07S 9/15
[52] U.S. Cl. .................................................. 558/077
[58] Field of Search ........................................ 558/77

[56] References Cited

U.S. PATENT DOCUMENTS

| | | | |
|---|---|---|---|
| 3,141,032 | 7/1964 | Friedman | 558/77 |
| 3,192,243 | 6/1965 | Gagliani | 558/77 |
| 3,325,566 | 6/1967 | Ratz et al. | 558/77 |
| 3,597,503 | 8/1971 | Wilson et al. | 558/84 |
| 3,819,748 | 6/1974 | Dulog et al. | 558/77 |
| 3,839,506 | 10/1974 | Hechenbleikner et al. | 558/77 |
| 3,846,317 | 11/1974 | Lintzenich | 252/46.7 |
| 3,978,167 | 8/1976 | Albright | 558/77 |
| 4,086,205 | 4/1978 | Birum | 558/77 |
| 4,154,721 | 5/1979 | Valdiserra et al. | 252/45.8 |
| 4,290,976 | 9/1981 | Hechenbleikner et al. | 558/77 |
| 4,341,722 | 7/1982 | Zinke | 558/85 |
| 4,348,291 | 9/1982 | Shim | 252/46.6 |
| 4,664,828 | 5/1967 | Juag et al. | 252/49.8 |

OTHER PUBLICATIONS

Computer Summary of CA70(1) 4074v.
Kosolapoff et al., "Organic Phosphorus Compounds", vol. 7, (1977), p. 531.

*Primary Examiner*—Anton H. Sutto
*Attorney, Agent, or Firm*—Emily A. Richeson

[57] ABSTRACT

A spirodiphosphoamidate-type composition is provided, wherein the composition is represented by the general formula:

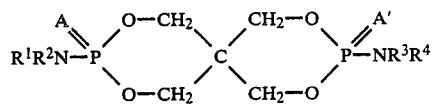

wherein A and A' are independently selected from the group consisting of oxygen and sulfur; $R^1$ and $R^3$ are independently selected from the group consisting of hydrogen, aliphatic, oxyaliphatic, polyoxyaliphatic, cycloaliphatic and aromatic moieties; and $R^2$ and $R^4$ are independently selected from the group consisting of $C_{13}$ and larger aliphatic, oxyaliphatic, polyoxyaliphatic and aliphatic substituted aryl groups.

4 Claims, 4 Drawing Sheets

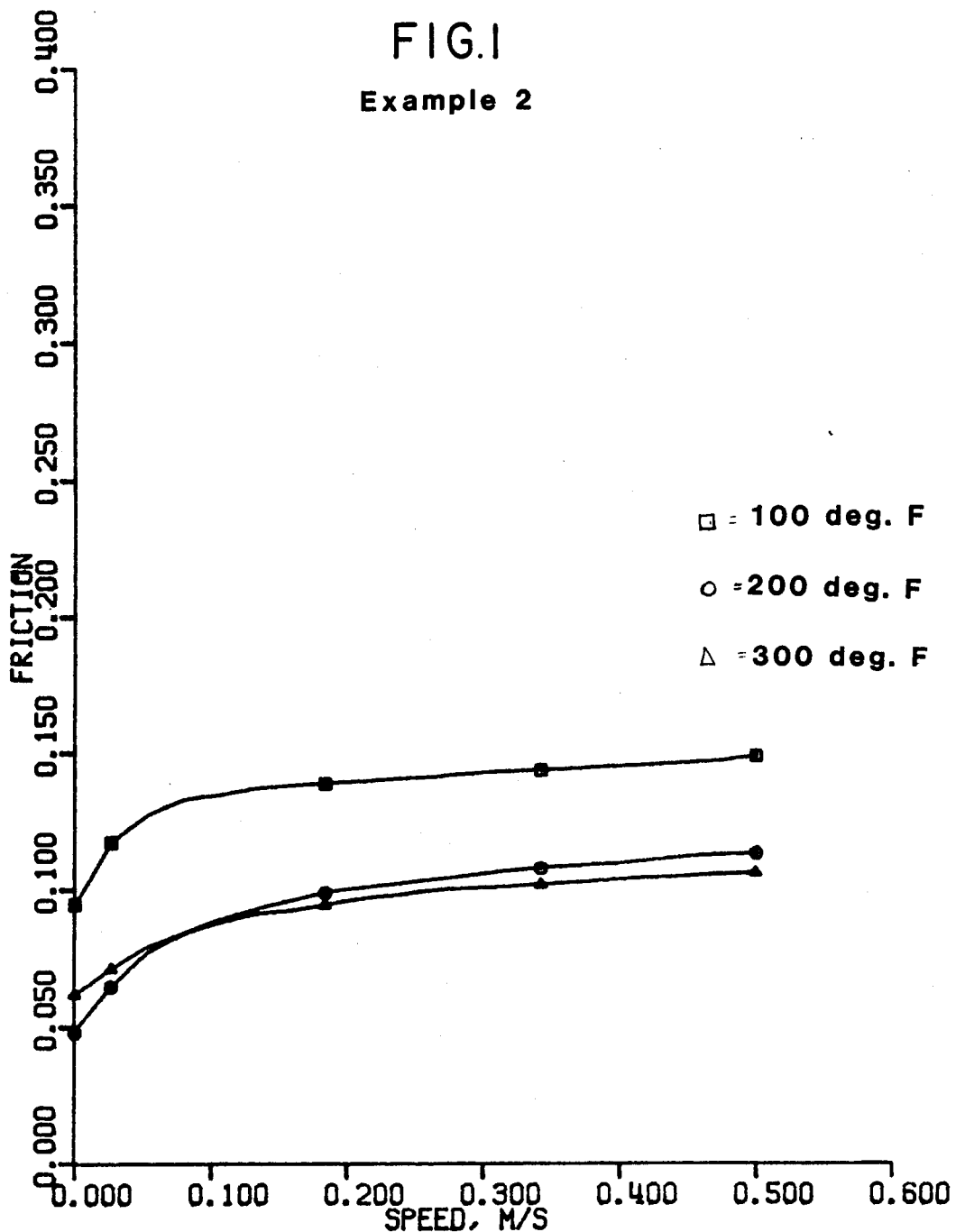

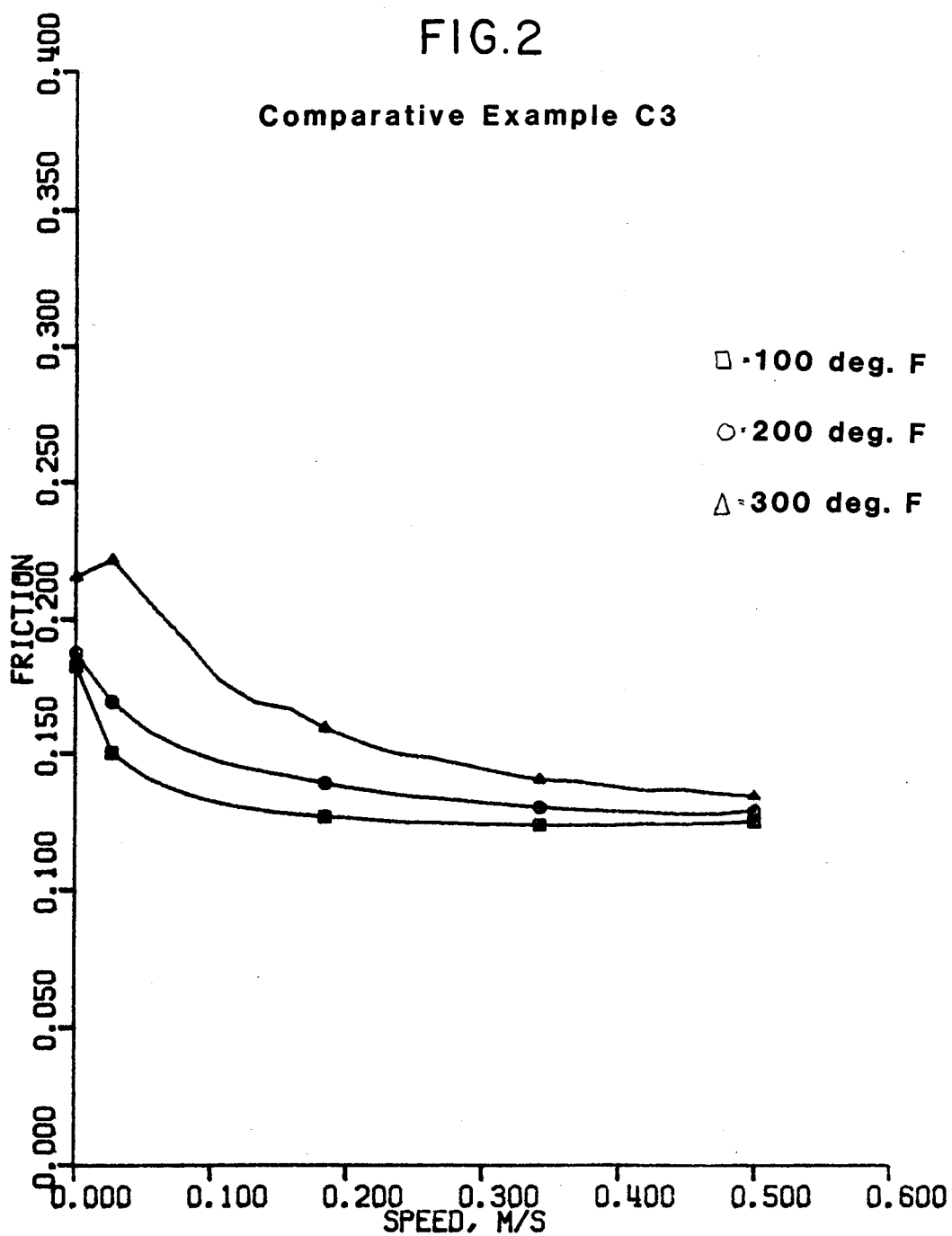

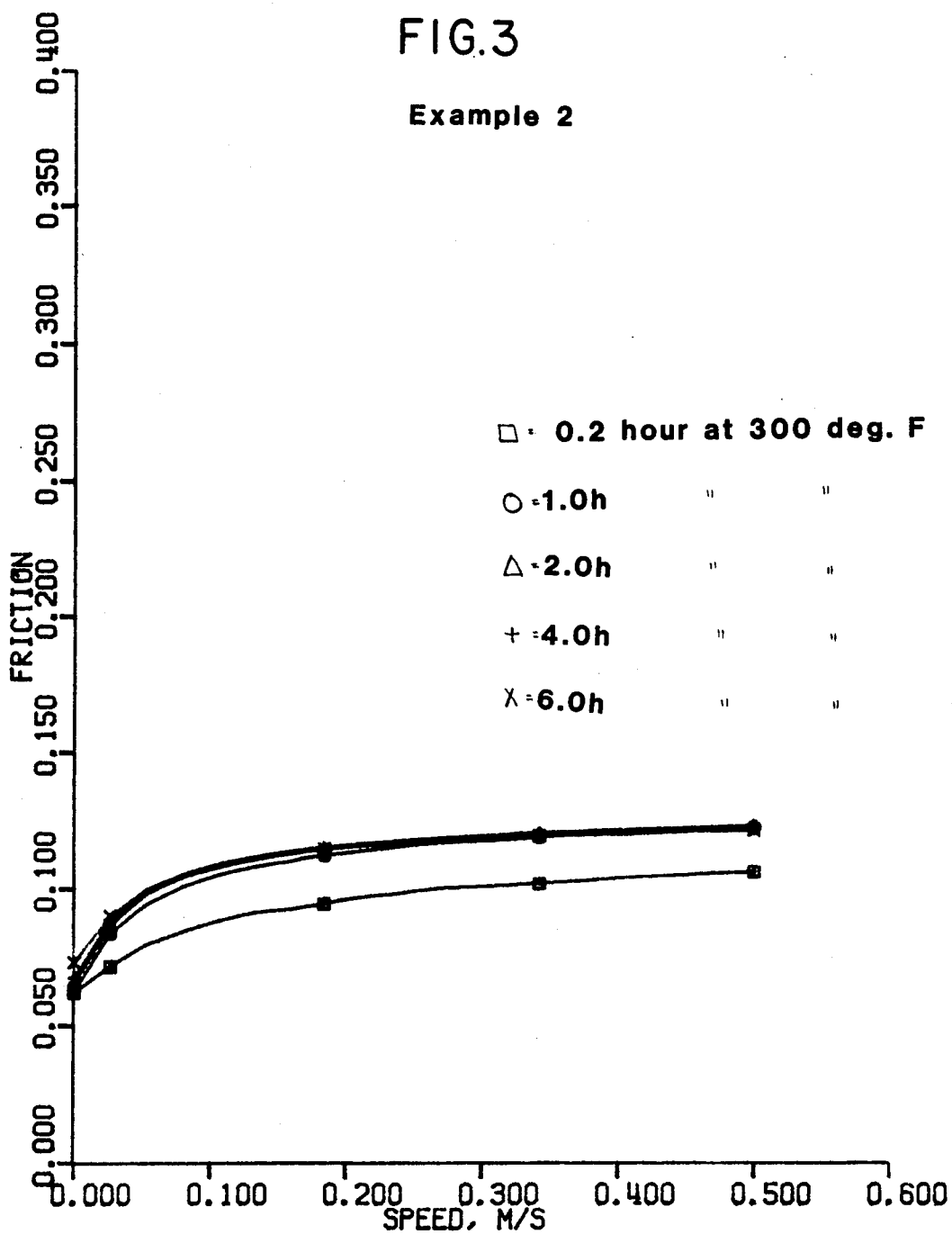

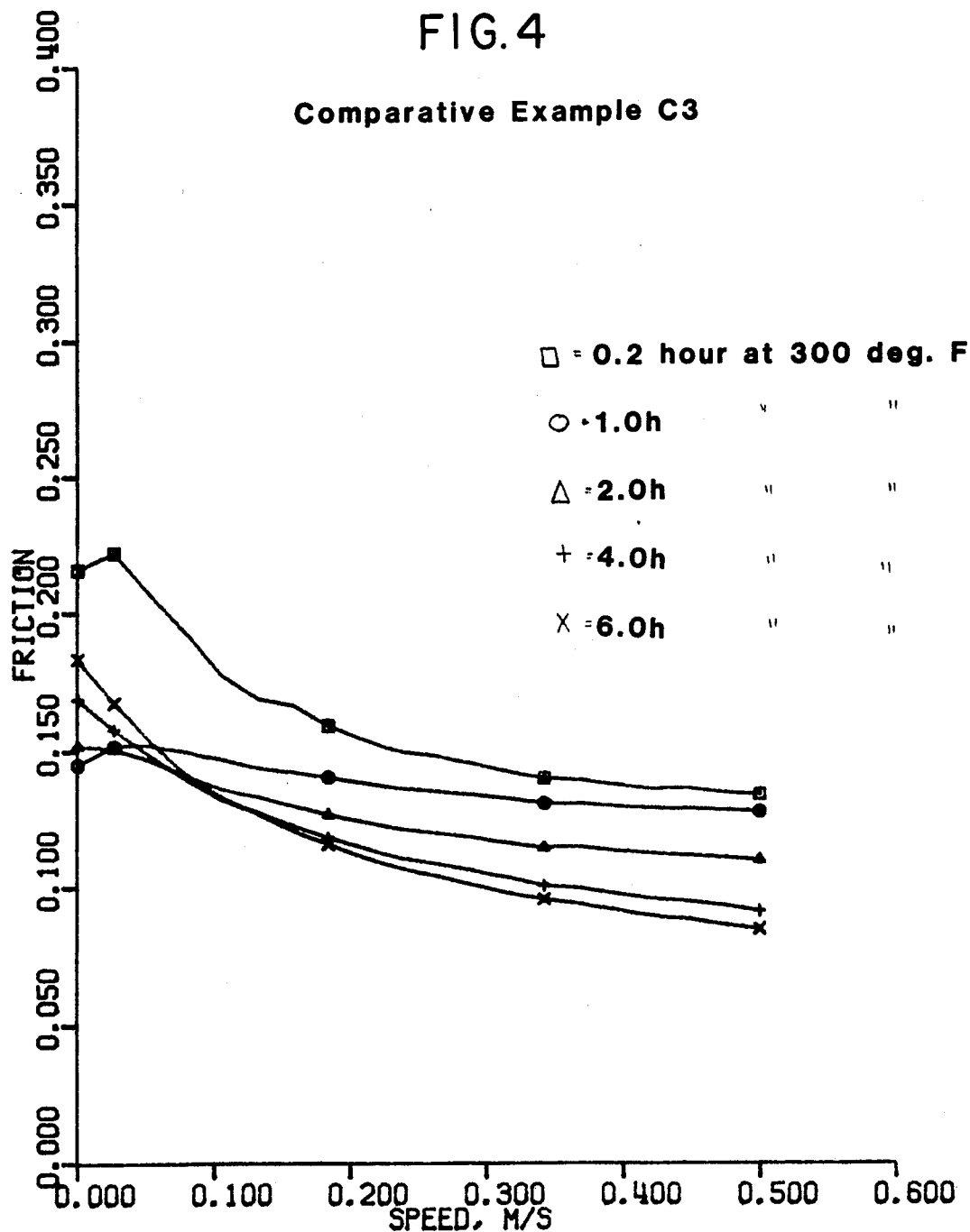

SPIRODIPHOSPHOAMIDATE COMPOUNDS

This application is a continuation of U.S. application Ser. No. 813,161, filed Dec. 24, 1985, now abandoned.

BACKGROUND OF THE INVENTION

The present invention relates in general to spirodiphosphoamidate-type compounds and to a process for their preparation.

Phosphoamidate compounds have a variety of practical uses, such as flame retardants, stabilizers or intumescent agents for coatings such as paints, antitumor agents, vulcanizing agents and additives to lubricant compositions.

Spirodiphosphoamidate-type compounds, including spirodiphosphoamidates and spirodithiophosphoamidates, are known in the art. U.S. Pat. No. 3,978,167 to Albright, discloses spirodiphosphoamidate-type compounds wherein the amino moiety may be substituted with one or more hydrocarbon groups of preferably not more than about 12 carbon atoms. Albright discloses these compounds may be useful as flame retardants or pesticides. Although Albright indicates the spirodiphosphoamidate may be a dithiophosphoamidate, oxygenated diphosphoamidate-type compounds are preferred.

Other spirodiphosphoamidate-type compounds, possibly useful as anti-tumor agents, are disclosed by Chemical Abstract 70(1):4074v. Phosphoamidates, useful in lubricating compositions, are disclosed by U.S. Pat. No. 4,348,291 to Shim and U.S. Pat. No. 3,846,317 to Lintzenich. However, these compounds may not perform as well as desired in applications such as automatic transmission fluids, cutting oils, lubricating greases and hydraulic fluids wherein maintenance of good lubricating properties under extreme pressure conditions is desired.

Several processes are known for the preparation of spirodiphosphate-type compounds. U.S. Pat. No. 3,978,167 to Albright discloses the reaction of dihalo pentaerythritol phosphate with a primary or secondary amine. U.S. Pat. No. 4,154,721 to Valdiserri et al discloses the reaction of pentaerythritol with an aryl dichlorophosphine to form a diaryl spiro-disphosphonite, followed by oxidation of the diphosphonite to the corresponding diarylspirodiphosphonate. U.S. Pat. No. 4,290,976 to Hechenbleikner et al discloses a process for preparing dialkylpentaerythritol diphosphites by contacting dichloropentaerythritol diphosphite with an alcohol. U.S. Pat. No. 3,325,566 to Ratz discloses dichlorospirodiphosphite may be converted to dihydrogen pentaerythitol dithiophosphate by reaction with hydrogen sulfide. Other processes for preparing phosphoamidates and similar compounds are disclosed by U.S. Pat. No. 3,846,317 to Lintzenich and U.S. Pat. No. 3,597,503 to Wilson et al.

However, many processes for preparing spirodiphosphate type compounds have the disadvantage of fostering significant ring opening side reactions, which lower the process yield. These processes may also have the disadvantage of requiring the use of relatively high temperatures, which may further encourage formation of by-products. Therefore, a process for preparing spiroddiphosphoamidate type compounds which suppresses ring opening and may be conducted at relatively moderate temperatures offers significant practical advantages over processes known in the art.

SUMMARY OF INVENTION

The present invention is directed to a spirodiphosphoamidate composition which is represented by the general formula:

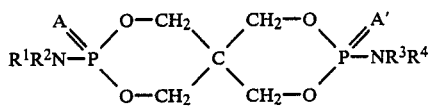

wherein A and A' are selected from the group consisting of oxygen and sulfur; $R^1$ and $R^3$ are selected from the group consisting of hydrogen, aliphatic, oxyaliphatic, polyoxyaliphatic, cycloaliphatic and aromatic groups; and $R^2$ and $R^4$ are selected from the group consisting of $C_{13}$ and larger aliphatic, oxyaliphatic, polyoxyaliphatic and aliphatic substituted aryl groups. Preferably, A and A' are sulfur, and $R^1$ and $R^3$ are selected from the group consisting of hydrogen, oxyaliphatic and polyoxyaliphatic groups. It is further preferred that $R^2$ and $R^4$ be selected from $C_{16}$ and larger groups.

The present invention also includes a process for making the composition of the present invention by reacting an amine with a dihalospirodiphosphite to form a spirodiphosphoamidite, followed by reacting the spirodiphosphoamidite with at least one of oxygen and sulfur to form the corresponding spirodiphosphoamidate.

BRIEF DESCRIPTION OF THE DRAWINGS

The present invention may be readily understood by reference to the following detailed description and the illustrative specific embodiments, considered in connection with the accompanying drawings wherein:

FIG. 1 graphically depicts the results of testing for Example 2 at 100° F., 200° F. and 300° F.;

FIG. 2 graphically depicts the results of testing for Comparative Example C3 at 100° F., 200° F. and 300° F.;

FIG. 3 graphically depicts the results of testing for Example 2 after 0.2, 1, 2, 4 and 6 hours at 300° F.; and FIG. 4 graphically depicts the results of testing for Comparative Example C3 after 0.2, 1, 2, 4 and 6 hours at 300° F.

DETAILED DESCRIPTION OF THE INVENTION

The present invention is a spirodiphosphoamidate-type composition represented by the general formula:

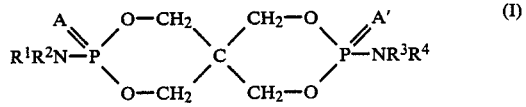

According to the invention, A and A' are selected from the group consisting of oxygen and sulfur. That is, the spirodiphosphoamidate-type composition may be a spirodiphosphoamidate or a spirodithiophosphoamidate. Although A and A' may be selected independently, such as when A is sulfur and A' is oxygen, A and A' are usually selected to be the same. Further, although A and A' may each be oxygen, such as in 3,9-bis(2,3-dibromopropoxy)-2,4,8,10-tetraoxa-3,9-diphosphaspiro(5.5)undecane-3,9-dioxide, it is preferred that both A and A' be sulfur, so that the composition is a spirodithiophoamidate.

Consistent with the invention, one of the substituents from each of the amino groups, $R^1$ and $R^3$ in formula (I) above, is selected from the group consisting of hydrogen, aliphatic, oxyalipatic, polyoxyaliphatic, cycloaliphatic and aromatic moieties, such as methyl, propyl, ethyl, butyl, hexyl, octyl, lauryl, cyclohexyl, oxyethyl, oxypropyl, poyoxyethylene, polyoxypropylene, p-tolyl, oleyl, phenyl, p-nonylphenyl, t-nonyl, p-methylphenyl and stearyl. Although $R^1$ and $R^3$ may be different, it is preferred that both $R^1$ and $R^3$ be selected to be the same. It is usually preferred that $R^1$ and $R^3$ be hydrogen. However, when water solubility is desired, it is preferred that at least one of $R^1$ and $R^3$ be selected from the group consisting of oxyaliphatic and polyoxyaliphatic moieties.

According to the invention, each of the amino groups has a substituent, $R^2$ and $R^4$ in formula (I) above, which is selected from the group consisting of $C_{13}$ and larger aliphatic, oxyaliphatic, polyoxyaliphatic or aliphatic substituted aryl moieties, such as myristyl, p-nonylphenyl, polyoxypropylene, polyoxyethylene, oxyoctadecanyl and stearyl. $C_{16}$ and larger aliphatic groups, such as oleyl, stearyl, lignoceryl, linoleyl, and arachidonyl, are more preferred. Alkenyl groups, such as oleyl and linoleyl, are further preferred.

The present invention also includes a process for making spirodiphosphoamidate-type compounds, and is particularly useful for making spirodithiophosphoamidates. This process comprises reacting an amine with a dihalospirodiphosphite to form a spirodiphosphoamidite. This spirodiphosphoamidite is reacted with at least one of oxygen and sulfur to form the corresponding spirodiphosphoamidate-type compound. As is apparent, when the spirodiphosphoamidite is reacted with oxygen or a peroxide, the corresponding compound will be a spirodiphosphoamidate; when the spirodiphosphoamidite is reacted with sulfur or a sulfur compound, the corresponding compound will be a spirodithiophosphoamidate.

The dihalospirodiphosphite preferably is dichlorospirodiphosphite. Dihalospirodiphosphites may be prepared by means known in the art, such as the reaction of phosphorus trichloride or other phosphorus trihalide with pentaerythritol.

The oxygen and sulfur may be in the elemental or molecular form, such as $O_2$ and elemental sulfur, or may be in the form of a compound, such as $H_2O_2$, t-butyl hydroperoxide and $H_2S$. However, $H_2O_2$ and elemental sulfur are preferred, with elemental sulfur being particularly preferred so that the compound formed is a spirodithiophosphoamidate. Preferably the molar ratio of oxygen or sulfur to spirodiphosphoamidite should be at least 2:1.

The identity of the amine will depend on the amino group sought to be obtained in the spirodiphosphoamidate compound. Under ordinary circumstances, a primary or secondary amine will be used, such as hexadecylamine, dioleylamine, myristylamine, oleylamine and stearylamine, so that the amine has one substituent which is hydrogen and two substituents which correspond to $R^1$ and $R^2$, or $R^3$ and $R^4$, respectively, in formula (I) above. Mixtures of different amines may be used, although preferably only one amine is used so that $R^1$ and $R^3$, and $R^2$ and $R^4$, respectively, are the same.

It is preferred that the molar ratio of amine to dihalospirodiphosphite be at least 2:1 to encourage complete substitution of the diphosphite. Greater ratios of 3:1, 4:1 or more may be used, although ratios in excess of about 2:1 are usually not preferred.

Conditions for reacting the amine with the dihalospirodiphosphite will vary depending, among other factors, on the amine used and whether a solvent, such as toluene, pyridine and ether, is present. Preferably, however, the amine is reacted with the dihalospirodiphospite at a temperature of up to about 50° C., assuming ambient pressure. Use of a tertiary amine, such as triethylamine, to scavenge hydrogen halide is recommended. Reaction of the spirodiphosphoamidite with oxygen or sulfur preferably should take place at a temperature of up to about 100° C., assuming ambient pressure.

SPECIFIC EMBODIMENTS

Preparation of a spirodiphosphoamidate composition of the present invention according to a process of the present invention is described below in Example 1.

EXAMPLE 1

Dichloro pentaerythritol spirodiphosphite (0.5M) was dissolved in toluene. This solution was added dropwise with stirring to a mixture of 236 g oleylamine (1.0M) and 94.7 g triethylamine (0.9M) at 0°–5° C. over a period of 1 hour. The mixture was stirred overnight at room temperature, and the resulting slurry filtered under nitrogen. The solid residue was washed thoroughly with toluene, and the toluene filtrates combined. Analysis by $^{31}P$ nuclear magnetic resonance spectroscopy (NMR) confirmed the presence of pentaerythritol spirodiphospho bis-oleylamidite in the filtrate.

Without purifying the filtrate solution, the pentaerythritol spirodiphospho bis-oleylamidite (0.25M) in toluene was added to 3 mL triethylamine. Elemental sulfur, 16 g (0.5M), was added with stirring. The temperature was increased to 41° C. and maintained for 1 hour. The mixture was filtered and the toluene solvent removed under vacuum. The structure of the remaining compound was confirmed by infrared spectroscopy, $^{31}P$ NMR, $^1H$ NMR and elemental analysis to be predominantly that of pentaerythritol spirodithiophospho bis-oleylamidate.

Samples (25 mL) of the compositions of Example 2 and Comparative Example C3 were evaluated on a Faville-La Vally low velocity friction tester using SD 715 friction material (annulus outer diameter 1.125 in., inside diameter 0.875 in., mean diameter 1.00 in.), running against SAE 1035 tumbled steel (1.500 in. diameter, 10–16 u in. AA surface finish) at 827 kilo Pascals (kPa) (120 psi). Frictional surfaces were initially broken in for 16½ hours. During break in and heating sequences the sliding speed was maintained at 0.2775 m/sec (50 ft/min).

EXAMPLE 2

As the composition of the present invention may be particularly useful in lubricants, the frictional characteristics and the thermal stability of a lubricating substance comprising a carrier medium, which was Citgo 150 neutral oil, and 0.25% weight of the compound prepared by the procedure described in Example 1 was tested as described above.

Testing was conducted at fluid temperatures of 100° F., 200° F. and 300° F. over sliding speeds of 0–0.5 m/sec. (0–100 ft/min.), and the friction measured.

The results of this testing are depicted graphically below in FIG. 1. These data indicated a reduction in friction at a low speed, with no significant increase in oxidation, which could detract from the composition's performance, at elevated temperatures. Friction reduction at low speeds is frequently important in reducing the torque required to start a mechanism moving. Reduced static friction also permits the smooth, chatter-free engagement of wet clutches, and may be a critical factor in whether a clutch permits smooth high speed shifting.

Changes in the friction characteristics of the composition of Examples 1 due to thermal degradation were also tested at 300° F. by measuring friction as a function of speed after maintaining the composition at 300° F. for 0.2, 1, 2, 4 and 6 hours. The rsults of this testing are depicted below in FIG. 3. These data also indicate that after some initial oxidation, further significant oxidation did not occur.

COMPARATIVE EXAMPLE C3

A working composition not embodying the present invention was tested according to the procedure described above for Example 2. The composition of Comparative Example C3 was Citgo 150 neutral oil without the spirodiphosphate additive. The results of testing of Comparative Example C3 at 100° F., 200° F. and 300° F. are shown graphically below in FIG. 2. These data indicated the comparative composition has higher friction at low speeds, and experiences some degradation of its properties, probably due to oxidation, at higher temperatures.

The results of testing the composition of Comparative Example C3 at 300° F. after maintaining the composition at 300° F. for 0.2, 1, 2, 4 and 6 hours are depicted graphically below in FIG. 4. These data also indicate higher friction at low speeds than the composition of Example 2. Although the sampled used for testing for Comparative Example C3 was not analyzed afterward, it is hypothesized the friction increase exhibited by the sample was due to the presence of polar oxidation products produced under the test conditions.

EXAMPLE 4

A composition consistent with the present invention was tested to assess its extreme pressure, antiwear and friction modifying properties. The carrier medium in the lubricating substance containing the composition was Citgo 150 neutral oil. Spirodithiophospho bis-oleylamidate, a composition consistent with one embodiment of the invention, was included.

The extreme pressure characteristics were measured by the Falex Method, ASTM No. D 3233-73 ("Standard Methods for Measurement of Extreme Pressure Properties of Fluid Lubricants.") Wear characteristics were tested by the Four-Ball Wear Test, ASTM No. D-2783. For each of these tests the amount of spirodithiophosphoamidate in the lubricating substance was 0.1 %wt phosphorus from the spirodithiophosphoamidate, based on 100 parts by weight Citgo neutral oil. The effect of the composition on static and dynamic friction was tested at 300° F. according to the procedure described above for the Low Velocity Friction Test. Static Friction in Table I was the lowest value measured at a slow creep speed. Dynamic Friction was the maximum value measured at 0.5 m/sec (100 ft/min). For the Low Velocity Friction Test the amount of spirodithiophosphoamidate in the lubricating substance was 0.25 %wt spirodithiophosphoamidate compound based on 100 parts by weight Citgo neutral oil. The results of this testing are indicated below in Table I.

COMPARATIVE EXAMPLES C5 AND C6

Two compositions not embodying the invention were tested as described above for Example 4 in Citgo 150 neutral oil. These compositions were spirodithiophospho-bis-laurylamidate and thiophospho oleylamidate. The structures of these compounds are shown below in Table I. The proportion of these thiophosphoamidates in the lubricating substances used in the Falax Extreme Pressure and The Four-Ball Wear Tests was 0.1 %wt phosphorus, based on the phosphorus in the thiophosphoamidate compounds and 100 parts by weight of Citgo neutral oil. The amount of thiophosphoamidate in the lubricating substances used for the Low Velocity Friction Test was 0.25 %wt based on 100 parts by weight of Citgo neutral oil. The results of this testing are indicated below in Table I.

COMPARATIVE EXAMPLE C7

A composition of only Citgo 150 neutral oil, without a spirodiphosphate additive, was tested as described above for Examples 4 and 5. The results of this testing are indicated below in Table I.

These data indicate that lubricating substances containing compositions of the present invention may exhibit superior extreme pressure, wear or friction characteristics in comparison to lubricants containing similar compounds not of the invention.

It will be understood that various changes and modifications may be made in the embodiments outlined above without departing from the spirit of the invention, which includes all equivalents and modifications thereof, and is limited only by the following claims.

TABLE I

| Example | Additive | Falex (lb.) | 4-Ball Scar diam. (mm) | Static Friction | Dynamic Friction | Static Dynamic |
|---|---|---|---|---|---|---|
| 4 |  | 1500 | 0.37 | 0.04 | 0.11 | 0.39 |
| C5 |  | 1250 | 0.37 | 0.05 | 0.13 | 0.39 |

TABLE I-continued

| Example | Additive | Falex (lb.) | 4-Ball Scar diam. (mm) | Static Friction | Dynamic Friction | Static Dynamic |
|---|---|---|---|---|---|---|
| C6 | $C_{18}H_{35}NH-P(=S)(O-)(O-)$ (cyclic) | 1000 | 0.46 | 0.07 | 0.13 | 0.54 |
| C7 | None | 300 | 0.76 | 0.20 | 0.13 | 1.53 |

What is claimed is:

1. A spirodiphosphoamidate-type composition represented by the general formula:

$$R^1R^2N-P(\!\!\begin{array}{c}A\\\end{array}\!\!)(\!\!\begin{array}{c}O-CH_2\\O-CH_2\end{array}\!\!)C(\!\!\begin{array}{c}CH_2-O\\CH_2-O\end{array}\!\!)P(\!\!\begin{array}{c}A'\\\end{array}\!\!)-NR^3R^4$$

wherein:

A and A' are independently selected from the group consisting of oxygen and sulfur;

$R^1$ and $R^3$ are independently selected from the group consisting of hydrogen, aliphatic, oxyaliphatic, polyoxyaliphatic, cycloaliphatic and aromatic moieties; and $R^2$ and $R^4$ are independently selected from the group consisting of $C_{16}$ and larger aliphatic, oxyaliphatic, polyoxyaliphatic and aliphatic substituted aryl groups.

2. The composition of claim 1 wherein A and A' are sulfur.

3. The composition of claim 1 wherein $R^1$ and $R^3$ are selected from the group consisting of oxyaliphatic and polyoxyaliphatic moieties.

4. The composition of claim 3 wherein $R^1$ and $R^3$ are hydrogen.

* * * * *